United States Patent [19]

Srivastava et al.

[11] Patent Number: 5,744,595
[45] Date of Patent: Apr. 28, 1998

[54] PROPARGYL MODIFIED NUCLEOSIDES AND NUCLEOTIDES

[75] Inventors: Suresh C. Srivastava, Burlington; Syed Kazim Raza, Waltham, both of Mass.

[73] Assignee: ChemGenes Corporation, Waltham, Mass.

[21] Appl. No.: 520,968

[22] Filed: Jul. 25, 1995

Related U.S. Application Data

[63] Continuation-in-part of PCT/US94/14429, Dec. 30, 1994, continuation-in-part of Ser. No. 176,481, Dec. 30, 1993, abandoned.

[51] Int. Cl.$^6$ .......................... C07H 19/67; C07H 19/10; C07H 19/167; C07H 19/20
[52] U.S. Cl. .................... 536/26.23; 536/25.34; 536/26.26; 536/26.6; 536/26.7; 536/26.71; 536/27.6; 536/27.81; 536/28.5; 536/28.53; 536/23.1; 536/24.3; 536/24.5
[58] Field of Search .................. 536/25.34, 26.23, 536/26.6, 26.1, 26.71, 27.6, 27.81, 28.5, 28.53, 26.26

[56] References Cited

U.S. PATENT DOCUMENTS 5,171,849  12/1992  Soloway et al. ............... 536/28.53

FOREIGN PATENT DOCUMENTS

| 0517262 | 12/1992 | European Pat. Off. . |
|---|---|---|
| 004198 | 1/1985 | Japan . |
| 174797 | 9/1985 | Japan . |
| 234020 | 10/1987 | Japan . |
| 1019691 | 4/1989 | Japan . |
| 9110671 | 7/1991 | WIPO . |
| 9310820 | 6/1993 | WIPO . |
| 9317717 | 9/1993 | WIPO . |

OTHER PUBLICATIONS

Sproat, et al., Nucleic Acids Research, vol. 19, No. 4, 1991, pp. 733–738.
Wu, et al., Tetrahedron, vol. 47, No. 12–13, 1991, pp. 2237–2254.
Froehler, et al., Tetrahedron Letters, vol. 34, No. 6, 1993, pp. 1003–1006.
Anisuzzaman, et al., Polyhedron, Vo., 9, No. 6, 1990, pp. 891–892.
Lesnik, et al., Biochemistry, vol. 32, No. 30, 1993, pp. 7832–7838.
Moris, et al., J. Org. Chem., vol. 58, No. 3, 1993, pp. 653–660.
Kumar, et al., Bull. Chem. Soc. Japan, vol. 65, No. 6, 1992, pp. 1665–1667.
Abusbeih, et al., Tetrahedron Letters, vol. 33, No. 33, 1992, pp. 4807–4810.
Beaucage, et al., Tetrahedron, vol. 48, No. 12, 1992, pp. 2223–2311.

*Primary Examiner*—Joe Kight
*Assistant Examiner*—L. Eric Crane
*Attorney, Agent, or Firm*—Hale and Dorr LLP

[57] ABSTRACT

The present invention describes a novel 2'-O-alkylation reaction to produce a novel series of nucleosides carrying the 2'-O-propargyl group, using propargyl bromide, dibutyl tin oxide and tetrabutyl ammonium bromide. The procedure involves novel techniques for regioselective introduction of 2'-/3'-O-propargyl group directly on the 5'-DMT-N-protected- nucleosides using dibutyl tin oxide as a mild base in conjunction with a phase transfer catalyst, tetrabutyl ammonium bromide. The reaction process has many significant features and leads to isomeric ratios in favor of the 2'-regio isomer. This allows the synthesis of the corresponding phosphoramidites of high purity.

8 Claims, 3 Drawing Sheets

PROPARGYL MODIFIED NUCLEOSIDES AND NUCLEOTIDES

CROSS-REFERENCE TO RELATED APPLICATIONS

This application is a continuation-in-part application, claiming priority to PCT/US94/14429, filed 30 Dec. 1994, and U.S. Ser. No. 08/176,481, filed 30 Dec. 1993, now abandoned.

FIELD OF INVENTION

This invention relates to the synthesis of propargyl modified nucleosides. The process for the introduction of propargryl modification is described for all the common ribonucleosides. The process is general in nature and has been utilized for the direct introduction of an allyl group into fully protected ribonucleosides. The modified nucleosides have been utilized to produce the corresponding phosphoramidites. Defined sequence DNA and RNA syntheses utilizing these products are made possible. The modified nucleosides, which are base- and sugar-protected, have led to the production of unprotected propargyl nucleosides.

BACKGROUND OF INVENTION

Antisense oligodeoxynUcleotides and oligoribonucleotides (ASOs) which are either gene-specific or messenger RNA specific are gaining overwhelming popularity for regulation and inhibition of genes and gene products. During the past year alone, there have been over 700 publications on sequence specific antisense oligonucleotide therapeutics. ASOs are being commonly used to elucidate structure—function in cell culture (1–10). (F. Cope, et al., *Proc. Natl. Acad., Sci. USA* 86:5590–5594 (1989); R. Heikkila, et al., *Nature* 328:445–449 (1987); A. Teichman-Weinberg, et al., *Gene* 72:297–307 (1988); C. Helene, et al., *Biochim. Biophys Acta* 1049:99–125 (1990); J. S. Cohen, *Oligonucleotides: Antisense Inhibitors of Gene Expression*, Macmillan/CRC Press, London/Miami; M. L. Stephenson, et al., *Proc. Natl. Acad., Sci., USA* 75:285–288 (1978); P. C. Zamecnik, et al., *Proc. Natl. Acad., Sci. USA* 75:280–284 (1978); M. Matsukura, et al., *Proc. Natl. Acad., Sci. USA* 86:4244–4248 (1989); C. C. Smith, et al., *Proc. Natl., Acad., Sci. USA* 83:2787–2791 ((1986); and J. A. Zaia, et al., *J. Virol.* 62:3914–3917 (1988)). ASOs have the potential of becoming a new class of pharmaceuticals by interacting with specific RNA or DNA sequences within cells. (G. Zon, *Pharmaceutical Res.* 5: 539–549 (1988) and W. B. Offensperger, *EMBO J.* 2:257 (1993)).

Some of the problems with ASOs are associated with their permeation into the cell nucleus. (N. Bischofberger and R. W. Wagner, *Semin. Virol.* 3:57 (1992)). One of the techniques used to solve this problem has been the microinjection method. (R. W. Wagner, et al., *Science* 260:510–513 (1993)). Another problem is that the modified oligomers are degraded both extracellularly, by serum nucleases, and intracellularly; their half-life in tissue culture is very short. Various approaches are therefore directed toward structural modifications for better permeability.

Various modifications of oligoribonucleotides have been carried out. The 2'-O-alkyl modification of oligoribonucleotides by introduction of 2'-O -alkyl group (Structure 8, R=CH₃, R=CH₂—CH=CH₂) has shown significant promise due to increased nuclease resistance, better membrane penetration and hybridizing capability. (E. Uhlmann and A. Peyman, *Chem. Rev.* 90:544 (1990)). The 2'-O-methyl oligoribonucleotides (Structure 8a, R=CH₃) exhibit high resistance to both DNA- and RNA-specific nucleases and form hybrids of high thermal stability with complementary RNA. (H. Inoue, et al., *Nucl. Acids Res. Syrup. Ser.* 6: 65–68 (1985); S. Shibahara, et al., *Nucl. Acids Res.* 5: 4403–4415 (1987); H. Inoue, et al., *FEBS Lett.* 25: 327–330 (1987); H. Inoue, *Nucl. Acids. Res.* 5: 6131–6148 (1987); B. Sproat, et at., *Nucleic Acids Res.* 7: 3373–3386 (1989); B. Sproat, et al., *Nucl. Acids Res.* 8: 41–49 (1990) and B. Beijer, et al., *Nucl. Acids Res.* 8: 5143–5151 (1990)). 2'-O-Allyl oligoribonucleotides (Structure 8b, R=CH₂—CH=CH₂) are superior ASOs as compared to 2'-O-methyl oligoribonucleotides in certain aspects, such as snRNP-mediated pre-mRNA splicing and processing. (A. Iribarren, et al., *Proc. Natl. Acad. Sci. USA* 87: 7747–7751 (1990); B. Sproat, et al., *Nucl. Acids Res.* 9: 733–738 (1991); A. Lamond, et al., *J. Cell:* 383–390 (1989); B. Blencowe, et al., *Cell* 59: 35–39 (1989); S. Barabino, et al., *EMBO J.* 8: 4171–4178 (1989); S. Barabino, et at., *Cell* 63: 293–302 (1990); U. Ryder, et al., *Nucl. Acids Res.* 8: 7373–7379 (1990) and M. Carmo-Fonseca, et al., *EMBO J.* 10: 193–206 (1991)). Similarly, sequence specific 2'-O-methyl (Structure 8a, R=CH₃) and 2'-O-ethyl oligoribonucleotides (Structure 8c, R=C₂H₅) complimentary to the 5'-end of U7-snRnp-RNA inhibit histone pre-mRNA processing in vitro at a very low concentration. (M. Cotten, et al., *Nucl. Acids Res.* 9: 2629–2635 (1991)). Other modifications include non-ionic methyl phosphonates and phosphothioates (J. P. Shaw, et al., *Nucleic Acids Res.* 9: 747–750 (1991) and C. C. Smith, et al., *Proc. Natl. Acad. Sci. USA* 83: 2787–2791 (1986)), phosphoramidates (S. Agarwal, et al., *Proc. Natl., Acad. Sci. USA* 85: 7079–7083 (1988)), ASOs conjugated to poly(L-lysine) (M. Lemaitre, et al., *Proc. Natl. Acad. Sci, USA:* 648–652 (1987)) and antibody-targeted liposomes containing ASOs. Similarly, ASOs covalently linked to phospholipid (R. G. Shea, et al., *Nucl. Acids Res.* 8: 3777–3783 (1990)), cholesterol (R. L. Letsinger, et al., *Proc. Natl. Acad. Sci. USA* 86: 6553–6556 (1989) and A. S. Boutorin, et al., *FEBS Lett* 254: 29–32 (1989)), dodecanediol (T. Saison-Behmoaras, et al., *EMBO J.* 10: 1–18 (1991)), undecyl residue (A. V. Kabonov, et al., *FEBS Lett.* 259: 327–330 (1990)) and thiocholesterol conjugates (B. Oberhauser, et al., *Nucl. Acids Res.* 20: 533–538 (1992)) have been designed. Thus strategic structural modifications of the sequence specific ASOs could be very useful in the development of an ideal ASO candidate.

Ideally, ASOs should have the following properties: (i) form hybrids of high thermal stability with complimentary target sequences; (ii) resistant to enzymatic degradation, but should not be infinitely stable, so it can be eliminated from the cell system after the desired effect has been achieved; (iii)should be able to inactivate RNAse activity surrounding the ASOs and target DNA or RNA sequences; and (iv) should be effective as ASOs at a low concentration and be sensitive to sequence mismatches. With these criteria, it seemed appropriate to design modifications in the mononucleoside, which could be suitably incorporated as part of an ASO, for superior performance.

The 2'-O-propargyl modification of nucleosides (Structures 2a-d and 3a–d), unknown prior to the present invention, has been achieved for all four nudeobases (A,C, G,U). The series has been further extended to the corresponding phosphoramidites (Structure 6a–d). A series of defined sequence oligonudeotides has been synthesized and purified to demonstrate that oligomers can be designed which have the 2'-modification at the specific and appropriate location (Structure 8d).

Among the alkylation methods, methyl iodide or allyl bromide in acetonitrile in the presence of the sterically hindered strong base 2-tert-butylimino-2-diethylamino-1,3 dimethyl perhydro- 1,2,3-diazaphosphorin (BDDDP) has been used (B. S. Sproat, et al., *Nucl. Acids Res.* 8: 4355 (1990) and U. Pieles, et al., *Nucl. Acids Res.* 8:4355 (1990)). However, the latter process involves chlorophenyl substituted purines in order to minimize purine ring alkylation side reactions. Another method which has been used recently involves Pd(O) catalyzed alkylation, for example with allyl ethyl carbonate, to obtain 2'-O-allyl substituted Structure 10 (B. S. Sproat, et al., *Nucleosides & Nucleotides* 10(1–3): 25–36 (1991) and German Patent No. P40 473.2). However, this procedure similarly involves chlorophenyl substituted pyrimidine and purine ring systems for the alkylation step. In subsequent steps this ring modification has to be converted back to natural pyrimidines and purines, thereby making the synthesis processes tedious and multistepped. Recently, 2'-/3'-O-allylation of uridine was achieved from allylbromide and dibutyl tin oxide as a mild base in conjunction with a phase transfer catalyst, tetrabutylammonium bromide. The reaction conditions, stoichiometry, etc., have not been optimized to lead to useful products. Thus, cytidine was converted to the 2'-O-allyl derivative (Structure 10b; C) indirectly from 2'-O-allyl uridine (Structure 10d; U) to 2'-O-allyl cytidine via transformation at the carbon atom at position 4 (C=O→C—$NH_2$) (V. Gopalakrishnan, et al., *Nucleosides and Nucleotides* 11(6): 263–273 (1992)).

SUMMARY OF INVENTION

The present invention successfully carries out the 2'-O-alkylation reaction to produce a novel series of nucleosides carrying the 2'-O-propargyl group, using propargyl bromide, dibutyl tin oxide and tetrabutyl ammonium bromide. The procedure involves novel techniques for regioselective introduction of 2'-/3'-O-propargyl group directly on the 5'-DMT-N-protected- nucleosides using dibutyl tin oxide as a mild base in conjunction with a phase transfer catalyst, tetrabutyl ammonium bromide. The reaction process has many significant features and leads to isomeric ratios in favor of the 2'-regio isomer. The single step process is applicable to all four commonly used bases (adenosine, cytidine, guanosine and uridine), making it extremely useful and valuable. Purification leads to final 2'-O-propargyl and 3'-O-propargyl isomers (Structures 2a–d and 3a–d) with very high purity (greater than 99%). This allows the synthesis of the corresponding phosphoramidites of high purity, such as Structures 6a–d.

The process of the invention is widely applicable and was successful with all the ribonucleosides tried in the present study. The generality of the process was further demonstrated by the synthesis of previously reported 5'-DMT-2'-O-allyl ribonucleosides of all four commonly known bases, A,C,G and U (Structures 4a–d and 5a–d), which were converted smoothly into the corresponding phosphoramidites (Scheme 3; Structure 7a–d). The rare phosphoramidites reported in this invention are thus obtained in a minimum number of synthesis steps possible. The availability of these phosphoramidites allows synthesis of DNA and RNA sequences which might possess unique biochemical properties. The nucleobases with the propargyl modification were synthesized as depicted in scheme 3. The aqueous ammonia smoothly removed the base protection. The product obtained was treated with aqueous acetic acid (80%) for a brief period (25 mins) to lead to nucleosides with the propargyl group (Scheme 4; Structures 9a–d). A large variety of oligonucleotides were synthesized using the modified bases. The preliminary data indicates that the propargyl modified oligomers have different rates of digestion with certain enzymes.

DETAILED DESCRIPTION OF THE INVENTION

The present invention is directed to nucleoside intermediates as shown in Structures 11 through 18.

In Structure 11:

Structure 12:

Structure 15:

and Structure 16:

Structure 17:

and Structure 18:

R¹ represents H, monomethoxytrityl, dimethoxytrityl, trimethoxytrityl, tetrahydropyranyl, a chromophore, a ligand, monophosphate, diphosphate or triphosphate;

R² represents H, OH or OH-protected with a removable group, such as silyl, tetrahydropyranyl, —OCOCH₂CH₂COOH, or a similar group for anchoring on solid supports and amenable to solid phase DNA or RNA synthesis, or an unremovable group, such as CH₃ or C₂H₅;

B represents the DNA or RNA bases, Adenine, Guanine or Cytosine, appropriately protected with a protecting group, or Thymine or Uracil, any of which may be structurally modified with various groups which can be used as chromophores or ligands;

R³ represents H, alkyl, aryl or hydrocarbonyl radical with or without electron attracting or donating groups;

R⁴ represents H, alkyl, aryl or hydrocarbonyl radical with or without electron attracting or donating groups;

R⁵ and R⁶ represent H, alkyl, aryl or hydrocarbonyl radical with or without electron attracting or donating groups;

R⁷ represents alkyl, cyanoethyl, or other phosphate protecting groups; and R⁸ and R⁹ represent alkyl or cyclic ring systems.

In Structure 13:

Structure 14:

B represents N-benzoyl adenine or N-isobutyryl guanine;

R¹ represents monomethoxytrityl, dimethoxytrityl, trimethoxytrityl, tetrahydropyranyl, a chromophore, a ligand, monophosphate, diphosphate or triphosphate;

R² represents H, OH or OH-protected with a removable group such as silyl or tetrahydropyranyl;

R³, R⁴ and R⁵ represent H, alkyl, aryl, or hydrocarbonyl radicals with or without electron attracting or donating groups;

R⁶ and R⁷ represent H, alkyl, aryl or hydrocarbonyl radical with or without electron attracting or donating groups;

R⁸ represents alkyl, cyanoethyl, or other phosphate protecting groups; and

R⁹ and R¹⁰ represent alkyl or combine to form a cyclic ring system.

The invention is further directed to DNA sequences represented by structures as in Structure 19:

wherein B represents DNA or RNA bases, Adenine, Guanine, or Cytosine, appropriately protected with a protecting group, or Thymine or Uracil, any of which may be structurally modified with groups which can be used as chromophores or ligands;

x represents O or S and y represents O, S or $CH_3$ (to make natural phosphate, phosphorothioates, phosphorodithioates, methyl phosphonates, methyl thiophosphonates or dithiophosphate);

R represents $CHR^3$—$C\equiv CR^4$, wherein $R^3$ and $R^4$ represent H, alkyl, aryl, or hydrocarbonyl radicals with or without electron attracting or donating groups; and $R^1$ and $R^2$ represent H, OH or other ligands or chromophores.

The following terms are defined herein: "chromophore" includes fluorescein and derivatives, rhodamine and derivatives, and biotin and biotin analogs; "ligand" includes cholesterol, digoxegenin, amino, carboxyl, aldehyde, and SH groups linked to the nucleoside via C-1 to C-15 carbon spacer; "other phosphate protecting groups" include methyl, trichloroethyl, p-nitrophenylethyl, o-chlorophenyl, cyanoethyl, and p-chlorophenyl; "alkyl group" includes methyl, ethyl, isopropyl, n-propyl, and other groups up to C-15; "a cyclic system" would include morpholino, piperidino, and other ring structures up to 15 atoms; "electron attracting groups" include fluoro, chloro, bromo, iodo, isocyano, cyano, acetamido, nitro, carboxyl esters, phenyl, chlorophenyl, and nitrophenyl; and "electron donating groups" include methyl, ethyl, propyl, isopropyl, butyl, isobutyl, pentyl, neopentyl, cyclohexyl, dimethylamino, diethylamino, diproprylamino, and diisopropylamino.

The invention is further directed to a method for the ini-roduction of the propargyl group $CHR^1$—$C\equiv CR^2$, or the allyl group, $CHR^3$—$CR^4$=$CR^5$, wherein $R^1$, $R^2$, $R^3$, $R^4$ and $R^5$ are H, alkyl, aryl or hydrocarbonyl radical with or without electron attracting or donating groups, in which the groups are added directly into a 5'- and N-protected ribonucleoside to obtain a 2'- and/or 3'- propargyl modification in the ribonucleoside or deoxynucleoside by using propargyl bromide or allyl bromide, respectively, DBTO and TBAB, as depicted in Scheme 1.

Finally, the invention is directed to a chemical or biological delivery system used for the delivery of DNA or RNA, incorporating chemically or encapsulating physically the propargyl-modified oligomer.

For the synthesis of 5'-DMT-2'-O-propargyl- (and 3'-O-propargyl) N-protected ribonucleosides, the following materials and methods were used.

The ultra violet spectra of the monomers, the trityl values and the OD units of the oligomers were obtained on the Shimadzu UV-1201 Spectrophotometer. The $^1H$ proton and $^{31}p$ phosphorus nuclear magnetic resonance spectra were obtained on a Varian XL-300 MHz Spectrometer equipped with a Varian 5 mm broad band probe. The $^1$H-NMR spectra were referenced to the internal $CHCl_3$ signal, and 1% TMS in the sample, 7.24 ppm and 0 ppm, respectively (Tables 1–3). $^{31}$P-NMR chemical shifts listed are downfield from 85% $H_3PO_4$, externally referenced. All the spectra were run in $CDCl_3$ (Cambridge Isotopes). $CDCl_3$ was also used as a lock reference in $^{31}$P-NMR analysis. DNA and RNA were synthesized on the Eppendorf Synostat D300 DNA-RNA Synthesizer. The DNA sequences were synthesized with standard protocols for defined sequence DNA synthesis (0.2 micromole scale). The HPLC analysis was done on the Rainin-Rabbit HPLC System with the Kipp and Zonen strip chart recorder and Altex 254 nm UV detector, and C-18 reverse-phase columns were used for the analyses. Propargyl bromide, dibutyl tin oxide (DBTO) and tetrabutyl ammonium bromide (TBAB) were purchased from Aldrich Chemical Co., Milwaukee, Wis. Gamma-$^{32}$P-ATP was obtained from Dupont New England Nuclear. All the enzymes were obtained from Boehringer-Mannheim, Ind.

Thin layer chromatography (tlc) was carried out on Baker-Flex silica gel IB-F TLC plates (20×20 cm and 5×20 cm). Column Chromatography was carried out using silica gel 60 (EM Science), particle size 0.04–0.063 mm (230–400 mesh), and particle size 0.063–200 mm (70–230 mesh).

Figure 1A:
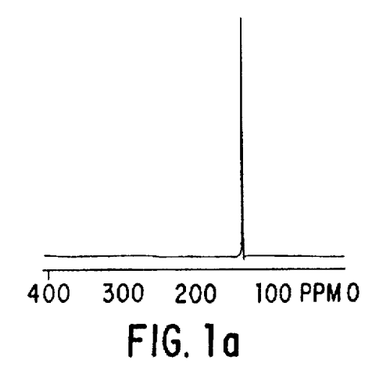
FIG. 1 shows the $^{31}p$ NMR spectra of 5'-DMT-2'-O-propargyl-3'-CNEt Phosphoramidites (Structures 6a–d).
Figure 1B:
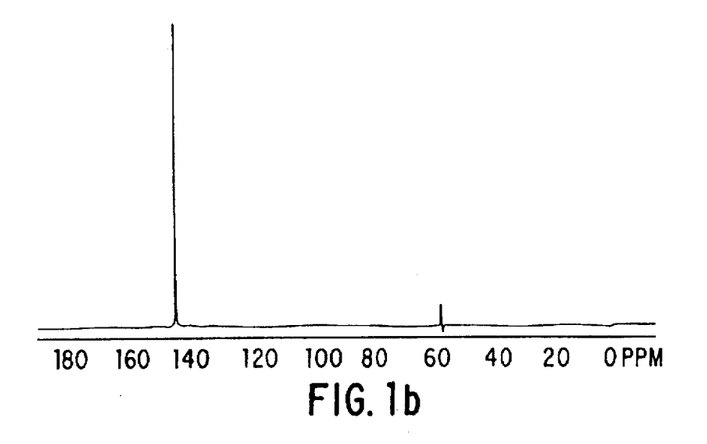
Figure 1C:
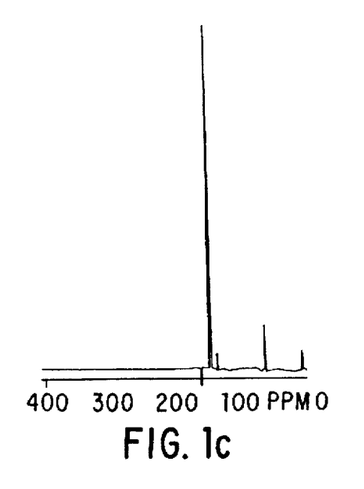
Figure 1D:
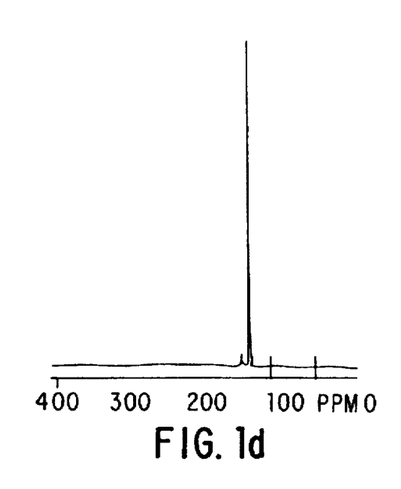
Figure 2:
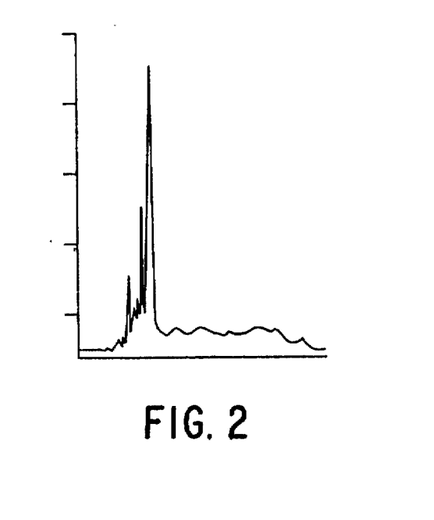
FIG. 2 shows the HPLC of Sequence #1, crude synthesized oligomer.
Figure 3:
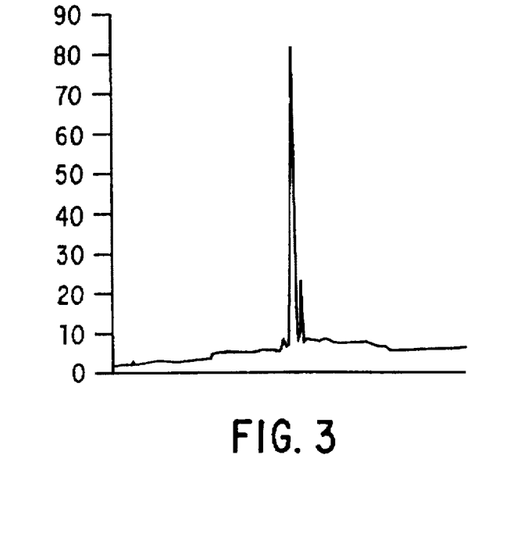
FIG. 3 shows the HPLC of Sequence #2, crude synthesized oligomer.
Figure 4:
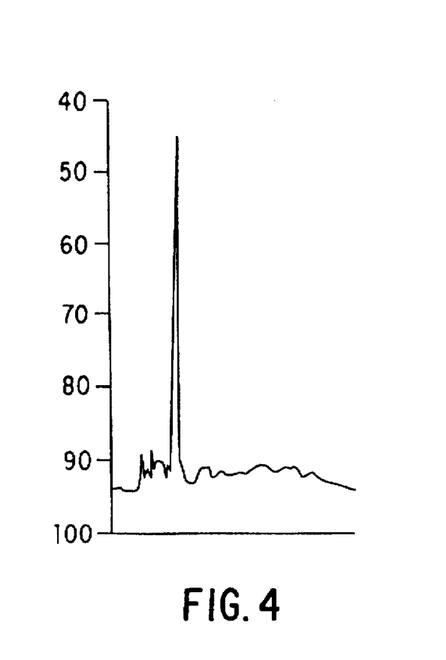
FIG. 4 shows the HPLC of Sequence #3, crude synthesized oligomer.
Figure 5:
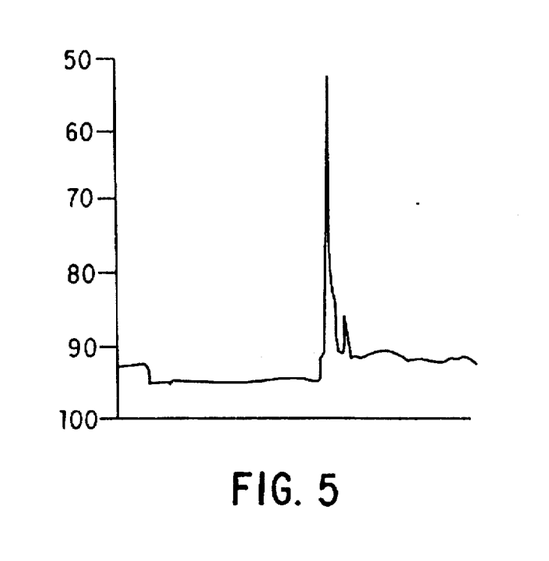
FIG. 5 shows the HPLC of Sequence #4, crude synthesized oligomer.
Figure 6:
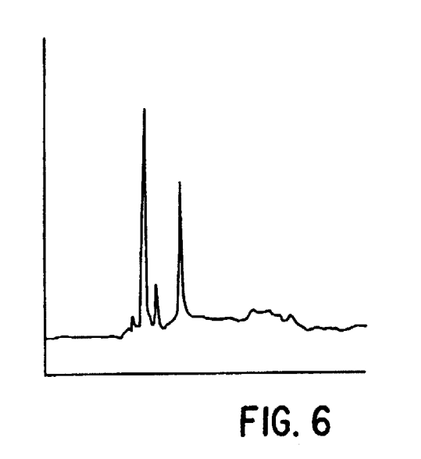
FIG. 6 shows the HPLC of Sequence #5a, crude synthesized oligomer.

For the determination of the detection limit and the establishment of purity of the propargyl nucleosides and the phosphoramidites (Structures depicted in Scheme I), tlc was used as the criteria. By using high conceneration, it was possible to detect impurities to the extent of 0.25%–0.10%. HPLC was used in conjunction with tlc. For the phosphoramidites, an additional purity parameter was $^{31}$P-NMR analysis. The desired phosphoramidite-associated peaks appear as sharp doublets (FIGS. 2 and 3 and Table 4). By taking up to a three-fold excess (as compared to the normal quantity of 16 mg) in $CDCl_3$, in the NMR tube and increasing the data acquisition time three times, it was possible to detect the impurities up to the extent of 0.5%.

EXAMPLE 1

Synthesis of 5'-DMT-2'-O-Propargyl- (and 3'-0-Propargyl-)

$N^6$-bz-Adenosine (Structures 2a and 3a)

A mixture of 5'-DMT-N6-bz-A (Structure 1a, 55.17 g; 80 mmol), TBAB (28.32 g; 88 mmol), DBTO (23.84 g; 96 mmol), and propargyl bromide (33.76 ml; 320 mmol), and dry DMF (225 ml), was stirred for 24 hrs at 40°–45° C. The mixture was then poured onto crushed ice. All the contents were filtered on a Buchner funnel. The gummy mass was dissolved in dichloromethane and the organic layer was washed with distilled water three times. Finally, the organic layer was passed through sodium sulfate and then concentrated and dried over high vacuum for four hours. The reaction reached completion to the extent of 50–60% as monitored by tlc. The crude reaction mixture was purified on silica gel column (1.5 kg, 230–400 mesh) using a gradient system of chloroform:hexane:acetone (50:40:10 to 50:30:20). The yield of pure 5'-DM T-2'-O-propargyl-$N^6$-bzA was 5.5 g (9.4%) and the regio-isomer 5'-DMT-3'-O-propargyl-N6-bzA was 2.3 g (4%). Other fractions containing varying proportions of isomers were not re-purified, and the total yields are unoptimized.

EXAMPLE 2

Synthesis of 5'-DMT-2'-O-Propargyl- (and 3'-0-Propargyl-)

$N^4$-bz-Cytidine Nucleoside (Structures 2b and 3b)

A mixture of 5'-DMT-N4-bzC (Stucture 1b, 23.29 g; 35 mmol), TBAB (12.39 g; 38.5 mmol), DBTO (10.43 g; 42 mmol), propargyl bromide (14.77 ml; 140 mmol), and dry DMF (100 ml) was stirred for 24 hrs at 40°–45° C. The mixture was then poured onto crushed ice. All the contents were filtered on a Buchner funnel. The gummy mass was dissolved in dichloromethane and the organic layer was washed with distilled water three times. Finally, the organic layer was passed through sodium sulfate and then concentrated, drying over a high vacuum for at least four hours. The reaction reached complet-ion up to 50–60% as monitored by tlc. The purification was done on a silica gel column (1.5 kg) using a solvent gradient system consisting of chloroform:hexane:acetone: methanol (50:30:20:0 to 50:30:10:2). The yield of pure 5'-DMT-2'-O-propargyl-N4-bzC was 4 g (16.23%), and the regio-isomer 5'-DMT-3'-O-propargyl-N4-bzC was 2.2 g (8.9%). Other fractions containing varying proportions of isomers were not re-purified and the total yields are unoptimized.

EXAMPLE 3

Synthesis of 5'-DMT-2'-O-Propargyl- (and 3'-O-Propargyl-)

$N^2$-ibu-Guanosine Nucleoside (Structures 2c and 3c)

A mixture of 5'-DMT-N2-ibuG (Structure 1c, 32.78 g; 50 mmol), TBAB (17.70 g; 35 mmol), DBTO (14.90 g; 60 mmol), propargyl bromide (42.2 ml; 200 mmol) and dry DMF (130 ml) was stirred for 24 hrs at 40°–50° C. The mixture was then poured onto crushed ice. All the contents were filtered on a Buchner funnel. The gummy mass was dissolved in dichloromethane and the organic layer was washed with distilled water three times. Finally, the organic layer was passed through sodium sulfate and then concentrated, dried over high vacuum for at least four hours. The reaction reached completion up to 40–50%, as monitored by tlc. The purification was done on a silica gel column (1 kg) using a solvent gradient system consisting of ethyl acetate:hexane: acetone:methanol (48:34:18:0 to 48:34:18:2). The product obtained from this column was repurified using a solvent gradient system consisting of chloroform:hexane:acetone:methanol (50:30:20:0 to 50:30:20:2). The yield of pure 5'-DMT-2'-O-propargyl-$N^2$-ibu-G was 4.25 g (12.25%), and the regio-isomer 5'-DMT-3'-O-propargyl-N2-ibuG was 3.2 g (9.2%). Other fractions containing varying proportions of isomers were not re-purified and the total yields were unoptimized.

EXAMPLE 4

Synthesis of 5'-DMT-2'-O-Propargyl-(and 3'-O-Propargyl-)

Uridine Nucleoside (Structures 2d and 3d)

A mixture of 5'-DMT-U (Structure 1d, 24.59 g; 45 mmol), TBAB (15.93 g; 49.5 mmol), DBTO (13.41 g; 54 mmol), propargyl bromide (18.99 ml; 180 mmol), dry DMF (100 ml) was stirred for 24 hours at 40°–50° C. The mixture was poured over crushed ice. All the contents were filtered over a Buchner funnel. The gummy mass was then dissolved in dichloromethane, and the organic layer was washed with distilled water three times. The organic layer was finally passed through $Na_2SO_4$. It was then concentrated and dried over high vacuum for at least four hours. The reaction reached completion up to 60–70%, as monitored by tlc. The purification of the crude product was carried out on a silica gel column (1.5 kg), using a solvent gradient system consisting of chloroform:ethyl acetate:triethylamine:methanol (45:45:8:2 to 44:44:8:4). The yield of pure isolated 5'-DMT-2'-O-propargyl-Uridine was 5 g (19%), and the regio-isomer 5'-DMT-3'-O-propargyl-Uridine was 3.6 g (13.7%). Other fractions containing varying proportions of isomers were not re-purified and the total yields were unoptimized.

EXAMPLE 5

Synthesis of 5'-DMT-2'-O-allyl- (and 3'-O-allyl-)

Nucleosides (Structures 4a–d and 5a–d)

These compounds were obtained similarly as outlined in Scheme 1, condition (ii), by the reaction of allyl bromide with the 5'-DMT-ribonucleosides (1a–d) in presence of DBTO and TBAB.

EXAMPLE 6

General Procedure for the Synthesis of 5'-DMT-2'-O-Propargyl-3'-Cyanoethyl

Phosphoramidite-Pyrimidine and Purine Nucleotides (Structures 6a–d)

The general phosphitylation conditions are described for the adenosine derivative, and they were followed for other bases in a similar manner.

5'-DMT-2'-O-propargyl-$N^6$-bzA (Structure 2a, 1 g; 1.4 mmol) was dissolved in dry chloroform (10 ml) containing N,N-diisopropyl ethylamine (1.2 ml, 9.37 mmol). To the solution was added beta-cyanoethyl-N,N-diisopropylaminophosphonamidic chloride (0.77 ml, 3.25 mmol) at 5° C. The mixture was stirred under argon atmosphere for 1.5 hour at room temperature. The solution was poured into a separatory funnel containing 70 ml EtOAc and extracted first by saturated $NaHCO_3$ solution and then by saturated NaCl. The organic layer was separated, dried over anhydrous $Na_2SO_4$ and concentrated to an oil in vacuum. The product was purified by column chromatography on silica gel. The product, 5'-O-DMT-2'-O-propargyl-3'-CNEt,N,N-diisopropyl N-bzA, obtained was 0.8 g (62.5% yield).

5'-DMT-2'-O-propargyl-N4-bzC (Structure 2b, 1.3 g, 1.89 mmol), chloroform (13 ml), N,N-diisopropyl ethyl amine (1.6 ml, 12.37 mmol) and the P-Cl reagent (1.03 ml, 4.347 mmol), were used to obtain 5'-DMT-2'-O-propargyl 3'-CNEt,N,N-diisopropyl-$N^4$-bzC under the above reaction conditions to yield 1 g (59.59%).

5'-DMT-2'-O-propargyl-$N^2$-ibuG (Structure 2c, 500 mg, 72 mmol), chloroform (5 ml), N,N-diisopropyl ethyl amine (0.548 ml, 4.278 mmol) and the P-Cl reagent (0.387 ml, 1.63 mmol) were taken to obtain 5'-DMT-2'-O-propargyl-3'-CNEt,N,N-diisopropyl-$N^2$-ibuG, under the above reaction conditions to yield 200 mg (31%).

5'-DMT-2'-O-propargylU (Structure 2d, 670 mg, 1.14 mmol), chloroform (7 ml), N,N-diisopropyl ethyl amine (0.998 ml, 7.79 mmol) and the P-Cl reagent (0.639 ml, 2.918 mmol) were taken to obtain 5'-DMT-2'-O-propargyl-3'-CNEt, N,N-diisopropyl-Uridine, under the above reaction conditions to obtain a yield of 150 mg (16.68%).

5-DMT-2'-O-allyl-3'-cyanoethyl phosphoramidites (Structures 7a–d) were synthesized as depicted in Scheme 3, and obtained with a protocol similar to that outlined for the nucleotide Structures 6a–d.

A large variety of oligonucleotides was synthesized using the modified bases. Some representative synthetic oligonucleotides containing O-propargyl modified bases are illustrated herein, and the feasibility of incorporation of 2'-O-propargyl modified phosphoramidites was demonstrated. The oligomer Sequences 4 and 5 were synthesized to compare digestion of similar sequence oligomers reported earlier with natural deoxy bases (23). Sequences 6, 7, 8 and 9 were synthesized to compare the data reported on same sequences with natural bases (44,45) for the targets located between the 5'-cap site and the tenth codon in the coding sequence of human c-myc mRNA, for suppressing the c-myc gene in cultured HL-60 cells.

Oligomer sequences (pro=2'-O-propargyl):
1. 5'-OHproA-proA-proA-proA-proA-dA-3'-OH
2. 5'-OHproC-proC-proC-proC-proC-dC-3'-OH 3. 5'-OHproU-proU-proU-proU-proU-dT-3'-OH
4. 5'-OH-proG-dA-dA-proC-dA-proG-dA-dT-dA-proC-dT-dA-proC-dA-proC-dT-dT-3'-OH (17-mer).
5a. 5'-OH-dG-dA-dA-dC-dA-dG-dA-proU-dA-dC-proU-dA-dC-dA-dC-proU-dT-3'-OH (17-mer).
5b. 5'-DMT-dG-dA-dA-dC-dA-dG-dA-proU-dA-dC-proU-dA-dC-dA-dC-proU-dT-3'-OH (17-mer with DMT-ON).
6. 5'OH-dG-dC-dC-dC-dC-dG-proA-proA-proA-proA-dC-dC-dG-dG-dC-3'-OH (15-mer.)
7. 5'OH-dG-proC-proC-proC-proC-dG-dA-dA-dA-dA-proC-proC-dG-dG-proC-dC-3'-OH
8. 5'-OH-dG-dC-dC-dC-dC-dG-proA-proA-proA-proA-dC-dC-dG-dG-proA-dC-3'-OH
9. 5'-OH-proG-dA-dA-proC-dA-proG-dA-dT-dA-proC-dT-dA-proC-dA-proC-dT-dT-3'-OH The syntheses were carried out 0.2 micromole scale on an Eppendorf Synostat D300 DNA/RNA synthesizer. The regular deoxynucleoside phosphoramidites as well as the propargyl modified phosphoramidites were used as 0.2M solution (80 ul per step) in anhydrous acetonitrile. The coupling time was 120 sec. throughout. The other synthesis protocols were same as time DNA synthesis parameters. The coupling efficiency for the propargyl modified bases was between 98.5% and 99.5% per step.

EXAMPLE 7

HPLC Purity Check and Purification of the Propargyl Modified Oligomers

Figure 7:
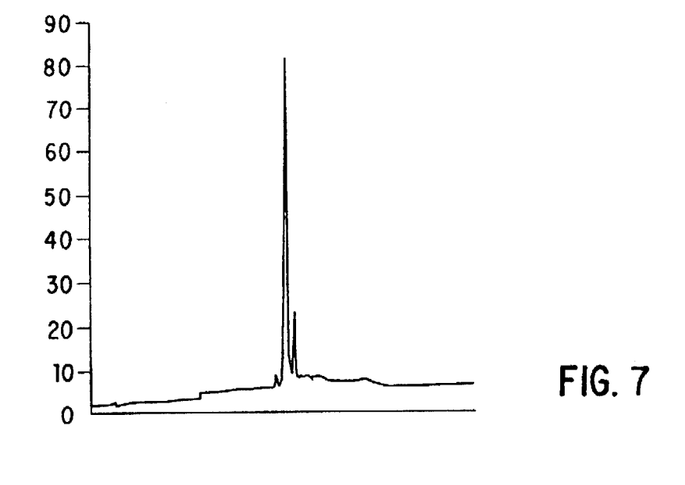
FIG. 7 shows the HPLC of Sequence #5b; the DMT-ON oligomer is peak B.
Figure 8:
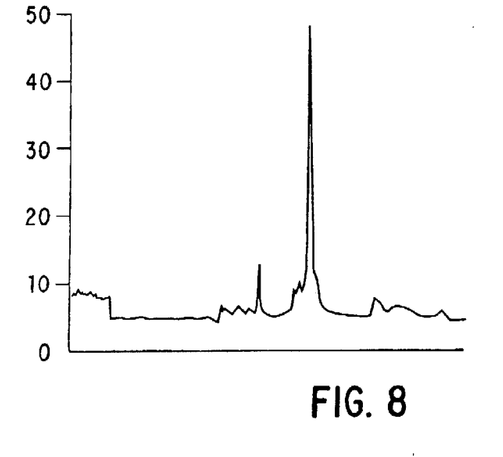
FIG. 8 shows the HPLC of Sequence #7, crude synthesized oligomer.
Figure 9:
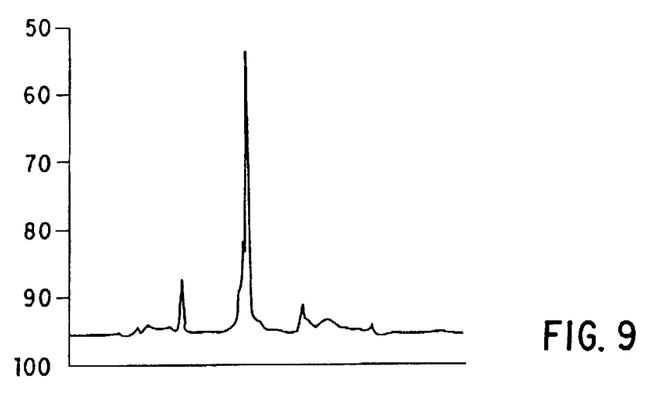
FIG. 9 shows the FIPLC of Sequence #8, crude synthesized oligomer.

Sequence #5b was purified on HPLC and the DMT-ON peak (peak B) was collected. This was then subjected to 80% aqueous acetic acid for 20 min at room temperature and further examined on HPLC; the pure, detritylated oligomer formation then takes place. All the oligomers after synthesis were examined on HPLC on a C-18 revers-e-phase column. In all cases, one major peak is observed in the 90–95% range.

EXAMPLE 8

End Labelling and Enzymatic Digestion of the Oligomers

A number of the oligomers obtained were end-labelled with gamma-$^{32}$P ATP and polynucleotide kinase under standard reaction conditions. All the oligomers incorporated the terminal phosphate to a high specific activity. Two additional oligodeoxynucleotides. Sequences #10 and #11 were used as controls. An oligomer containing internal modifications with 2'-O-methyl-riboadenosine was synthesized (Sequence #12) with a sequence otherwise identical to Sequence #8. The end labelling was performed after protecting group removal and lyophilization. An autoradiogram showed these crude modified oligomers to be of 90–95% purity, similar to what was observed on HPLC. The oligomers used for enzymatic digestion were passed on P-2 gel to remove the inorganic phosphates, and the fractions containing the desired band were lyophilized. Digestion was carried with Bal 31. Bxonuclease III, mung bean nuclease. P1 nuclease. S1 nuclease and snake venom phosphodiesterase enzymes on a number of selected oligomers.

The consol DNA sequences used were as follows:

Sequence #10: 5'-OH-dG-dC-dC-dC-dC-dG-dA-dA-dA-dA-dC-dC-dG-dG-dC-dC-3'-OH (16 mer);

Sequence #11: 3'-OH-dG-dC-dC-dC-dC-dG-dA-dA-dA-dA-dC-dC-dG-dG-dA-dC-3'-OH (16 mer);

The control DNA sequence incorporating 2'-OMe nucleotides was:

Sequence #12: 5'-OH-dG-dC-dC-dC-dC-dG-mA-mA-mA-mA-dC-dC-dG-dG-mA-dC-3'-OH, where mA is 2'-OMe Adenosine.

The preliminary data indicates that the propargyl modified oligomers have different rates of digestion with certain enzymes.

Although the foregoing invention has been described in some detail by way of illustration and example for the purposes of clarity and understanding, it will be obvious to one skilled in the art that certain changes and modifications may be practiced within the scope of the appended claims.

Scheme 1

(i) Propargyl bromide, DBTO, TBAB
(ii) Allyl bromide, DBTO, TBAB

Scheme 2

Structure 6
a; bz adenine
b; bz cytosine
c; ibu guanine
d; uracil (i) β-Cyanoethyl-N,N-diisopropylamino phosphonamidic chloride

Scheme 3

Structure 7
a; bz adenine
b; bz cytosine
c; ibu guanine
d; uracil (i) β-Cyanoethyl-N,N-diisopropylamino phosphonamidic chloride

Scheme 4

Structure 8

8a; R; $CH_3$

8b; R; $CH_2-CH=CH_2$

8c; R; $C_2H_5$

8d; R; $CH_2-C\equiv CH$

15

Structure 9 a; Adenine b; Cytosine c; Guanine d; Uracil (i) aqueous ammonia 8–10 hours @ Room temp (ii) 80% aqueous acetic acid for 25 minutes.

16

Structure 10 b; Cytosine d; Uracil

TABLE I

Rf values of various Propargyl derivatives:
(A) 5'-OH-2'-O-propargyl Nucleosides (9a–d)

| | Solvent Systems | | |
|---|---|---|---|
| | Chloroform | Methanol | Rf |
| 2'-O-propargyl Adenosine (9a) F.W.: 305.29 | 80 | 20 | 0.60 |
| 2'-O-propargyl Cytidine (9b) F.W.: 265.26 | 80 | 20 | 0.20 |
| 2'-O-propargyl Guanosine (9c) F.W.: 321.29 | 70 | 30 | 0.38 |
| 2'-O-propargyl Uridine (9d) F.W.: 282.25 | 80 | 20 | 0.30 |

(B) 5'-DMT-N-protected (2'- & 3'-)-O-propargyl Nucleosides (2a–d & 3a–d):

| | Solvent Systems | | | | 2'-isomer | 3'-isomer |
|---|---|---|---|---|---|---|
| | Ethyl acetate | Chloroform | Triethyl amine | Methanol | (2a–d) Rf | (3a–d) Rf |
| 5'-DMT-N6-bz- propargyl Adenosine F.W.: 711.738 | 47 | 47 | 6 | — | 0.46 | 0.36 |
| 5'-DMT-N4-bz- propargyl Cytidine F.W.: 687.710 | 47 | 47 | 6 | — | 0.50 | 0.24 |
| 5'-DMT-N2-ibu- propargyl Guanosine F.W.: 692.718 | 44 | 44 | 8 | 4 | 0.45 | 0.33 |
| 5'-DMT- propargyl Uridine F.W.: 584.590 | 46 | 46 | 8 | — | 0.37 | 0.27 |

Rf values for various propargyl derivatives:
(C) 5'-DMT-N-protected-(2'-)-O-propargyl Phosphoramidites (6a–d):

| | Solvent Systems | | | |
|---|---|---|---|---|
| | Ethyl acetate | Hexane | Triethyl amine | Rf |
| 5'-DMT-N-bz-2'-O- propargyl Adenosine-3'-CNEt phophoramidite (6a) F.W.: 911.963 | 60 | 30 | 10 | 0.64 0.55 |
| 5'-DMT-N-bz-2'-O- propargyl Cytidine-3'-CNEt phosphoramidite (6b) F.W; : 887.933 | 60 | 30 | 10 | 0.55 0.45 |
| 5'-DMT-2'-O-propargyl-Uridine- 3'-CNEt phosphoramidite (6d) F.W.: 784.815 | 60 | 30 | 10 | 0.64 0.55 |

TABLE I-continued

| | Dichloro methane | | Acetone | | |
|---|---|---|---|---|---|
| 5'-DMT-N-ibu-2'-O-propargyl Guanosine-3'-CNEt phosphoramidite (6c) F.W.: 892.943 | 37 | 37 | 10 | 16 | 0.58 |

TABLE II $^1$H-NMR Spectral Data of 5'-DMT-2'-(& 3'-)-O-Propargyl-N-protected Ribo Nucleosides (2a–d) & (3d)

| H-1' | H-2' | H-3' | H-4' | H-5' & 5" | DMT | Aromatic | CH$_2$—C≡C | C—CH | C≡CH | CH$_3$\C/CH$_3$ | H-2 | H-5 | H-6 | H-8 |
|---|---|---|---|---|---|---|---|---|---|---|---|---|---|---|
| \multicolumn{15}{c}{5'-Dimethoxytrityl-2'-O-propargyl-N6-bz-Adenosine (2a):} |
| 6.24 | 4.58 | 4.91 | 4.26 | 3.39 | 3.78 | 6.75 | 4.36 | | 2.40 | | 8.25 | | | 8.74 |
| — | — | — | — | — | — | — | — | | — | | — | | | — |
| 6.25 d,J; 5.07 | 4.61 | 4.94 t | 4.28 | 3.56 | | 7.71 | 4.38 dd | | 2.41 t | | — s | | | — s |
| \multicolumn{15}{c}{5'-O-Dimethoxytrityl-2'-O-propargyl-N4-bz-Cytidine (2b):} |
| 6.00 | 4.16 | 4.11 | 4.07 | 3.58 | 3.83 | 6.87 | 4.66 | | 2.47 | | | 7.19 | 8.56 | |
| — | — | — | — | — | — | — | — | | — | | | — | — | |
| s | 4.17 | 4.14 | 4.10 | 3.61 m | — s | 7.63 | 4.70 t | | 2.49 t | | | 7.23 | 8.58 d,J; 7.51 | |
| \multicolumn{15}{c}{5'-O-Dimethoxytrityl-3'-O-propargyl-N4-bz-Cytidine (3b):} |
| 5.98 | 4.45 | — | 4.29 | 3.43 | 3.81 | 6.83 | 4.49 | | 2.42 | | | 7.33 | 8.40 | |
| — | — | — | — | — | — | — | — | | — | | | — | — | |
| d | | 4.32 | 4.31 | 3.58 m | 3.81 d,J; 7.08 | 7.65 | 4.52 m | | 2.44 t | | | 7.35 J = 7.01 | 8.42 d,J; 7.08 | |
| \multicolumn{15}{c}{5'-O-Dimethoxytrityl-2'-O-propargyl-N2-ibu-Guanosine (2c):} |
| 5.91 | 4.60 | 5.08 | 4.24 | 3.15 & 3.19 | 3.76 | 6.77 | 4.19 & 4.23 | 1.73 | 2.41 | 0.75 | | | | 7.86 |
| — | — | — | — | — | — | — | — | — | — | — | | | | — |
| 5.93 d J; 6.65 | 4.62 dd J; .33 | 5.12 dd | 4.25 m | 3.51 & 3.55 m | — | 7.55 | 4.30 & 4.36 m | 1.77 m | 2.43 m — | 0.97 | | | | s |
| \multicolumn{15}{c}{5'-O-Dimethoxytrityl-2'-O-propargyl Uridine (2d):} |
| 5.97 | 4.23 | 4.48 | 4.04 | 3.53 | 3.80 | 6.79 | 4.43 | | 2.50 | | | 5.27 | 7.99 | |
| — | — | — | — | — | — | — | — | | — | | | — | — | |
| 5.98 | 4.25 | 4.49 | 4.07 | 3.54 | — | 7.45 | 4.56 | | 2.52 | | | 5.29 & 5.30 | 8.02 | |
| J; 2.50 | J; 7.70 | — | — | — | — | — | — | | — | | | J;9.85 | J; 8.11 | |
| d | dd | | m | s | s | — | m | | — | | | dd | d | |
| \multicolumn{15}{c}{5'-O-Dimethoxytrityl-3'-O-propargyl Uridine (3d):} |
| 5.93 | 4.39 | 4.389 | 4.21 | 3.41 | 3.80 | 6.82 | 4.25 | | 2.45 | | | 5.36 | 7.83 | |
| — | — | — | — | — | — | — | — | | — | | | — | — | |
| 5.94 J; 2.95 | 4.39 — | 4.392 — | 4.23 — | 3.57 — | — | 7.45 — | 4.29 — | | 2.46 J;8.07 | | | 5.39 J;7.57 | 7.85 — | |
| d | s | s | s | — | — | — | m | | — | | | d | d | |

TABLE III $^1$H-NMR Spectral Data of 5'-DMT-2'-O-propargyl-3'-CNEt Phosphoramidites (6a-d):

5'-Dimethoxytrityl-2'-O-propargyl-N6-bz-Adenosine-3'-Cyanoethyl,N,N-diisopropyl Phosphoramidite (6a):

| H-1' | H-2' | H-3' | H-4' | H-5' & H-5" | DMT | Aromatic | CH$_2$-C≡C | C≡CH | P-O-CH$_2$ | CH$_2$CN | N-H-C | N-C(CH$_3$)(CH$_3$) | H-5 | H-6 |
|---|---|---|---|---|---|---|---|---|---|---|---|---|---|---|
| 6.22 | 4.61 | 5.09 | 4.26 | 3.32 | 3.77 | 6.74 | 4.32 | 2.28 | 3.52 | 2.36 | 2.63 | 1.06 | 6.99 | 8.53 |
| — | — | — | — | — | — | — | — | — | — | — | — | — | — | — |
| 6.24 | 4.69 | 5.12 | 4.28 | 3.42 | 3.78 | 7.62 | 8.36 | 2.32 | 3.54 | 2.41 | 2.69 | 1.20 | 7.10 | 8.62 |
| dd | m | — | m | m | d | — | m | m | m | — | — | m | dd | dd |

5'-Dimethoxytrityl-2'-O-propargyl-N4-bz-Cytidine-3'-Cyanoethyl,N,N-diisopropyl Phosphoramidite (6b):

| H-1' | H-2' | H-3' | H-4' | H-5' & H-5" | DMT | Aromatic | CH$_2$-C≡C | C≡CH | P-O-CH$_2$ | CH$_2$CN | N-H-C | N-C(CH$_3$)(CH$_3$) | H-5 | H-6 |
|---|---|---|---|---|---|---|---|---|---|---|---|---|---|---|
| 6.06 | 4.42 | 4.30 | 4.23 | N/A | 3.826 | 6.85 | 4.54 | 2.50 | 3.46 | 2.37 | 2.62 | 0.99 | — | 7.83 |
| — | — | — | — | — | — | — | — | — | — | — | — | — | — | — |
| 6.08 | 4.51 | 4.36 | 4.26 | N/A | 3.831 | 7.89 | 4.68 | 2.57 | 3.94 | 2.45 | 2.66 | 1.29 | — | 7.86 |
| d | — | — | — | — | — | — | — | — | — | — | — | — | — | d |

5'-Dimethoxytrityl-2'-O-propargyl-N2-ibu-Guanosine-3'-Cyanoethyl, N,N-diisopropyl-Phosphoramidite (6c):

| H-1' | H-2' | H-3' | H-4' | H-5' & H-5" | DMT | Aromatic | CH$_2$-C≡C | C≡CH | P-O-CH$_2$ | CH$_2$CN | N-H-C | C-CH(CH$_3$)(CH$_3$) | N-C(CH$_3$)(CH$_3$) | H-8 |
|---|---|---|---|---|---|---|---|---|---|---|---|---|---|---|
| 5.84 | 4.59 | 4.25 | 4.21 | 3.76 | 3.798 | 6.80 | 4.22 & 4.25 | 2.31 | N/A | N/A | 0.89 | 1.68 | 0.75 & 0.78 | — |
| — | — | — | — | — | — | — | — | — | — | — | — | — | — | — |
| 5.96 | 4.60 | 4.28 | 4.31 | 3.77 | 3.803 | 7.56 | 4.30 & 4.37 | 3.34 | N/A | N/A | 1.29 | 1.90 | 0.87 & 0.89 | — |
| dd | m | m | — | — | — | — | — | m | — | — | — | — | — | — |

5'-Dimethoxytrityl-2'-O-propargyl-Uridine-3'-Cyanoethyl Phosphoramidite (6d):

| H-1' | H-2' | H-3' | H-4' | H-5' & H-5" | DMT | Aromatic | H-5 | H-6 | CH$_2$-C≡C | C≡CH | P-O-CH$_2$ | CH$_2$CN | N-H-C | N-C(CH$_3$)(CH$_3$) |
|---|---|---|---|---|---|---|---|---|---|---|---|---|---|---|
| 6.02 | 4.34 | 4.50 | 4.21 | 3.56 | 3.798 | 6.80 | 5.23 | 7.94 | 4.40 | 2.56 | 3.43 | 2.39 | 2.64 | 1.02 |
| — | — | — | — | — | — | — | — | — | — | — | — | — | — | — |
| 6.06 | 4.39 | 4.63 | 4.31 | 3.62 | 3.803 | 7.43 | 5.30 | 8.02 | 4.44 | 2.63 | 3.76 | 2.45 | 2.68 | 1.37 |
| m | — | d,m | — | — | — | — | Quad | Quad | — | — | — | — | — | — |

TABLE IV

¹H-NMR Spectral Data of 2'-O-Propargyl Nucleosides (9a–d):

2'-Propargyl-Adenosine (9a):

| H-1' | H-2' | H-3' | H-4' | H-5' & H-5" | CH₂—C≡C | C≡CH | H-2 | H-8 |
|------|------|------|------|-------------|---------|------|-----|-----|
| 6.05 | 4.40 | 4.71 | 4.10 | 3.61 | 4.21 | 2.54 | 8.08 | 8.25 |
| — | — | — | — | — | — | — | — | — |
| 6.07 | 4.42 | 4.74 | 4.11 | 3.78 | 4.24 | 2.56 | — | — |
| d | — | — | m | m | — | — | s | s |
| J = 6.6 | — | — | — | — | — | — | — | — |

2'-Propargyl-Cytidine (9b):

| H-1' | H-2' | H-3' | H-4' | H-5' & H-5" | H-5 | H-6 | CH₂—C≡C | C≡CH |
|------|------|------|------|-------------|-----|-----|---------|------|
| 5.88 | 4.18 | 4.02 | 3.95 | 3.69 | 5.78 | 7.99 | 4.46 | 2.57 |
| — | — | — | — | — | — | — | — | — |
| 5.89 | 4.19 | 4.04 | 3.98 | 3.88 | 5.80 | 8.01 | — | 2.58 |
| d | s | — | — | — | d | d | — | — |
| — | — | — | — | — | J = 7.5 | J = 7.4 | — | — |

2'-Propargyl-Uridine (9d):

| H-1' | H-2' | H-3' | H-4' | H-5' & H-5" | H-5 | H-6 | CH₂—C≡C | C≡CH |
|------|------|------|------|-------------|-----|-----|---------|------|
| 5.95 | 4.20 | 4.33 | 4.16 | 3.68 | 5.59 | 8.01 | 4.96 | 2.57 |
| — | — | — | — | — | — | — | — | — |
| 5.96 | 4.24 | 4.34 | 4.17 | 3.78 | 6.61 | 8.04 | 5.05 | — |
| d | d | — | — | m | d | d | m | s |
| J = 4.2 | — | — | — | — | J = 8.11 | J = 8.06 | — | — | s = sharp single; d = doublet; dd = doublet of doublet; m = multiplet; Quad = quadruplet; N/A = Not available due to interference

TABLE V

| Structure # | Upfield Peak | Downfield Peak | Δ (in Hertz) |
|-------------|--------------|----------------|--------------|
| 31p NMR Spectral Data of 5'-DMT-2'-O-propargyl-3'-CNEt Phosphoramidites (6a–d): | | | |
| A (6a) | 145.181 | 145.741 | 0.559 |
| C (6b) | 145.127 | 145.238 | 0.111 |
| G (6c) | 144.528 | 145.175 | 0.647 |
| U (6d) | 146.000 | 146.090 | 0.090 |
| 31p NMR Spectral Data of 5'-DMT-2'-O-allyl-3'-CNEt Phosphoramidites (7a–d): | | | |
| A (7a) | 145.780 | 146.333 | 0.553 |
| C (7b) | 144.930* | | |
| G (7c) | 144.684 | 144.935 | 0.251 |
| U (7d) | 144.940* | | |

*: Only one peak observed.

We claim:

1. A compound having the formula wherein B represents the DNA or RNA bases, Adenine, Guanine or Cytosine, each optionally protected with a protecting group, or Thymine or Uracil; $R^1$ represents H, monomethoxytrityl, dimethoxytrityl, trimethoxytrityl, tetrahydropyranyl, a chromophore, a ligand, monophosphate, diphosphate or triphosphate;

$R^2$ represents H; OH; OH-protected with silyl, tetrahydropyranyl, —OCOCH₂CH₂COOH, or another removable group capable of anchoring on solid supports and amenable to solid phase DNA or RNA synthesis; or OH-protected with CH₃, C₂H₅ or another unremovable group;

$R^3$, $R^4$, $R^5$ and $R^6$ each represent H; or alkyl, aryl or hydrocarbonyl radical, each with optional electron attracting or electron donating substituent groups;

$R^7$ represents alkyl, cyanoethyl, or another phosphate protecting group; and $R^8$ and $R^9$ each represent alkyl or together form a cyclic structure.

2. The compound of claim 1 wherein $R^3$, $R^4$, $R^5$ and $R^6$ each represent H, $R^7$ represents cyanoethyl, and $R^8$ and $R^9$ each represent isopropyl.

3. A compound having the formula wherein B represents the DNA or RNA bases, Adenine, Guanine or Cytosine, each optionally protected with a protecting group, or Thymine or Uracil; $R^1$ represents H, monomethoxytrityl, dimethoxytrityl, trimethoxytrityl, tetrahydropyranyl, a chromophore, a ligand, monophosphate, diphosphate or triphosphate;

$R^2$ represents H; OH; OH-protected with silyl, tetrahydropyranyl, —OCOCH₂CH₂COOH, or another removable group capable of anchoring on solid supports and amenable to solid phase DNA or RNA synthesis; or OH-protected with $CH_3$, $C_2H_5$ or another unremovable group; and $R^3$, $R^4$, $R^5$ and $R^6$ each represent H; or alkyl, aryl or hydrocarbonyl radical, each with optional electron attracting or electron donating substituent groups.

4. The compound of claim 3, wherein $R^3$, $R^4$, $R^5$ and $R^6$ each represent H.

5. A compound having the formula wherein B represents N-benzoyl adenine or N-isobutyryl guanine;

$R^1$ represents monomethoxytrityl, dimethoxytrityl, trimethoxytrityl, tetrahydropyranyl, a chromophore, a ligand, monophosphate, diphosphate or triphosphate;

$R^2$ represents H, OH or OH-protected with silyl, tetrahydropyranyl or another removable group;

$R^3$, $R^4$, $R^5$, $R^6$ and $R^7$ each represent H; or alkyl, aryl, or hydrocarbonyl radicals, each with optional electron attracting or electron donating substituent groups;

$R^8$ represents alkyl, cyanoethyl, or another phosphate protecting group; and $R^9$ and $R^{10}$ each represent alkyl or together form a cyclic system.

6. The compound of claim 5 wherein $R^3$, $R^4$, $R^5$, $R^6$, $R^7$ each represent H, $R^8$ represents cyanoethyl and $R^9$ and $R^{10}$ each represent isopropyl.

7. A compound having the formula wherein B represents N-benzoyl adenine or N-isobubyryl guanine;

$R^1$ represents monomethoxytrityl, dimethoxytrityl, trimethoxytriiyl, tetrahydropyranyl, a chromophore, a ligand, monophosphate, diphosphate or triphosphate;

$R^2$ represents H, OH or OH-protected with silyl, tetrahydropyranyl or another removable group; and $R^3$, $R^4$, $R^5$, $R^6$ and $R^7$ each represent H; or alkyl, aryl, or hydrocarbonyl radicals, each with optional electron attracting or electron donating substituent groups.

8. The compound of claim 7, wherein $R^3$, $R^4$ $R^5$, $R^6$ and $R^7$ each represent H.

* * * * *

UNITED STATES PATENT AND TRADEMARK OFFICE
CERTIFICATE OF CORRECTION

PATENT NO. : 5,744,595
DATED : April 28, 1998
INVENTOR(S) : Suresh C. Srivastava and Syed K. Raza It is certified that error appears in the above-identified patent and that said Letters Patent is hereby corrected as shown below:

In claim 3, page 22, lines 51-59, the portion of the structure reading $R^4C\equiv\!\equiv\!R^3CO$    should read    $R^4C\equiv\!\equiv\!C\text{-}R^3CO$ Signed and Sealed this Fourteenth Day of September, 1999

Attest:

Q. TODD DICKINSON

*Attesting Officer*            *Acting Commissioner of Patents and Trademarks*